US009675647B2

(12) United States Patent
Uchida et al.

(10) Patent No.: US 9,675,647 B2
(45) Date of Patent: *Jun. 13, 2017

(54) PROPHYLACTIC AND/OR THERAPEUTIC AGENT FOR FUNCTIONAL GASTROINTESTINAL DISORDERS

(75) Inventors: Masayuki Uchida, Kanagawa (JP); Shigeru Yamato, Chiba (JP); Hajime Ariga, Chiba (JP); Hirotsugu Uehara, Chiba (JP); Tomofumi Amano, Chiba (JP); Keiko Morikubo, Kanagawa (JP); Kaori Yoshida, Kanagawa (JP)

(73) Assignee: MEIJI CO., LTD., Tokyo (JP)

( * ) Notice: Subject to any disclaimer, the term of this patent is extended or adjusted under 35 U.S.C. 154(b) by 876 days.

This patent is subject to a terminal disclaimer.

(21) Appl. No.: 12/523,010

(22) PCT Filed: Jan. 17, 2008

(86) PCT No.: PCT/JP2008/050515
§ 371 (c)(1),
(2), (4) Date: Aug. 19, 2009

(87) PCT Pub. No.: WO2008/088008
PCT Pub. Date: Jul. 24, 2008

(65) Prior Publication Data
US 2010/0040698 A1    Feb. 18, 2010

(30) Foreign Application Priority Data

Jan. 17, 2007 (JP) .................... 2007-007628

(51) Int. Cl.
*A61K 35/74* (2015.01)
(52) U.S. Cl.
CPC .................... *A61K 35/74* (2013.01)
(58) Field of Classification Search
None
See application file for complete search history.

(56) References Cited

U.S. PATENT DOCUMENTS

| 7,374,915 B2 | 5/2008 | Sato et al. |
| 2004/0005304 A1 | 1/2004 | Brudnak |
| 2004/0170617 A1 | 9/2004 | Finegold |
| 2006/0093651 A1 | 5/2006 | Nagai et al. |
| 2008/0194688 A1 | 8/2008 | Sato et al. |

FOREIGN PATENT DOCUMENTS

| EP | 1738761 A1 | 1/2007 |
| JP | 8-098677 A | 4/1996 |
| JP | 2005-508617 A | 4/2005 |
| JP | 2006-501281 A | 1/2006 |
| KR | 2006/0130721 A | 12/2006 |
| WO | WO 01/28547 A1 | 4/2001 |
| WO | WO 03/016544 A1 | 2/2003 |
| WO | WO 2005/030229 A1 | 4/2005 |
| WO | WO 2005/099725 A1 | 10/2005 |

OTHER PUBLICATIONS

Colomban et al., Biotechnology and Bioengineering, vol. 42, pp. 1091-1098 (1993).*
Kajander et al. Aliment Pharmacol Ther 2005; 22: 387-394.*
Uchida et al. , J Pharmacol Sci. Dec. 2005;99(4):329-34.*
Ara, K., "Propionic Acid Bacteria no Kagaku," *New Food Industry*, Nov. 2003, vol. 45, No. 11, pp. 58-64.
Harasawa, Integrated Handbook of Internal Medicine, Progress 8 Shokakan Shikkan, 1997, vol. 51.
Kajander, K. et al., "A probiotic mixture alleviates symptoms in irritable bowel syndrome patients: a controlled 6-month intervention," *Aliment Pharmacol Ther*, Sep. 2005, vol. 22, No. 5, pp. 387-394.
Kajander, K. et al., "Clinical studies on alleviating the symptoms of irritable bowel syndrome with a probiotic combination." *Asia Pac J Clin Nutr*, 2006, vol. 15, No. 4, pp. 576-580.
Uchida, M. et al., "Efficacy of the Bifidogenic Growth Stimulator (BGS) Produced by *Propionibacterium freudenreichii* ET-3," *Foods and Food Ingredients Journal of Japan*, 2005, vol. 210, No. 12, pp. 1132-1140.
Drossman, D.A., "The Functional Gastrointestinal Disorders and the Rome II Process" *Gut*, vol. 45, pp. II1-II5.
Heitkemper, Margaret and Monica Jarrett (Jan. 2001) "'Its's Not All in Your Head': Irritable Bowel Syndrome" *American Journal of Nursing* 101(1):26-34.
Lembo, Anthony and Michael Camilleri (Oct. 2, 2003) "Chronic Constipation" *N. Engl. J. Med.* 349:1360-1368.
"Inflammatory Bowel Disease and Irritable Bowel Syndrome—Similarities and Differences," *Crohn's & Colitis Foundation of America*, www.ccfa.org, Jul. 2014, pp.1-12.

* cited by examiner

*Primary Examiner* — Irene Marx
(74) *Attorney, Agent, or Firm* — Saliwanchik, Lloyd & Eisenschenk

(57) ABSTRACT

The present inventors conducted dedicated studies, and as a result discovered that propionic acid bacteria fermentation products have a preventive/therapeutic effect on functional gastrointestinal disorders in in vitro tests and tests using patients with irritable bowel syndrome, and completed the present invention. Specifically, the present inventors discovered, in in vitro tests, that the products have an effect of increasing the intestinal contraction frequency without changing the intestinal contractile force in a distal colon-specific manner. Moreover, effects of improving the defecation condition, general abdominal condition, and health-related QOL in patients with irritable bowel syndrome were also found. Furthermore, propionic acid bacteria fermentation products can be taken in large amounts. Therefore, the propionic acid bacteria fermentation products can be expected to have an effect of preventing/treating functional gastrointestinal disorders safely.

4 Claims, 5 Drawing Sheets

SUMMARY OF THE FOUR WEEKS

※ DEGREE OF GENERAL IMPROVEMENT:
COMPARED TO BEFORE INGESTION
(4 WEEKS AGO)

- ☐ CONSIDERABLY IMPROVED
- ☐ IMPROVED
- ☐ NO CHANGE
- ☐ WORSENED
- ☐ CONSIDERABLY WORSENED (PLEASE CHOOSE ONE)

※ COMPARISON BETWEEN EARLY AND LATE PERIODS:
COMPARED TO THE TABLET OF THE EARLY PERIOD

- ☐ BETTER IN THE EARLY PERIOD
- ☐ NO CHANGE
- ☐ BETTER IN THE LATE PERIOD (PLEASE CHOOSE ONE)

FIG. 3

PROPHYLACTIC AND/OR THERAPEUTIC AGENT FOR FUNCTIONAL GASTROINTESTINAL DISORDERS

This application is a National Stage Application of International Application Number PCT/JP2008/050515, filed Jan. 17, 2008; which claims priority to JP 2007-007628, filed Jan. 17, 2007, which are incorporated herein by reference in their entirety.

TECHNICAL FIELD

The present invention relates to agents for preventing and/or treating functional gastrointestinal disorders, food for preventing and/or treating functional gastrointestinal disorders, and uses of fermentation products by propionic acid bacteria in the production thereof.

BACKGROUND ART

Functional gastrointestinal disorders (FGIDs) are a group of gastrointestinal disorders not including organic diseases (colon cancer, ulcerative colitis, Crohn's disease, amebic dysentery, and such). FGIDs are caused by abnormalities of gastrointestinal functions such as motor and sensory functions, and develop various symptoms such as abdominal pain, nausea, vomiting, bloating sensation, and defecation trouble such as constipation and diarrhea, depending on the affected area.

FGIDs include a total of 25 diseases: six esophageal diseases, three gastroduodenal diseases, five intestinal diseases, two abdominal pains, two biliary tract diseases, three rectal/anal diseases, and four of the pediatric area. Of these, for example, diseases whose main symptom is constipation are the following two diseases, when the pediatric area is excluded: (constipation-type) irritable bowel syndrome (IBS) and functional constipation (FC).

FGIDs do not affect life prognosis. However, FGIDs reduce the quality of life (QOL) and increase medical expenses, and thus have a significantly unfavorable impact on the society.

In the last decades, significant advances have been made in the study of organic diseases, and even malignant tumors are no longer being called incurable diseases. On the other hand, studies on functional abnormalities of the gastrointestinal tract still remain immature. The prevalence of FGIDs is predicted to further increase in the 21st century which is called high-stress society. Thus, elucidation of the pathogenesis of FGIDs and the development of novel therapies are important objectives for the future.

Irritable bowel syndrome (IBS), which is included in FGIDs, is caused by functional abnormalities of the lower digestive tract, and its pathophysiology is known to be motility abnormalities of the intestines, mainly of the colon. The observed symptoms include abdominal pain, abdominal discomfort (characterized by being relieved by defecation), defecation abnormalities (diarrhea, constipation, and combination of diarrhea and constipation), abnormal stool form (inclusion of mucus and abnormal hardness), and sense of abdominal bloating. The intestinal transit time is shortened in the diarrhea type, while the time is prolonged in the constipation type. Although the area and contractile pattern differ, an enhanced intestinal motility state is observed in both types. It is reported that, as compared to healthy individuals, IBS patients show abnormal responses to stress, stimuli such as diet, and cholinergic agents. It is also known that the perception threshold to the rectal or ileocecum balloon distension is lower (Non-Patent Document 1).

Conventionally known agents for improving constipation symptoms include those that bloat the stool with water to improve the stool property and induce a desire to defecate (bulk-forming laxatives) and those that directly promote the intestinal movement, in particular, the intestinal contractile force (stimulant laxatives). Stimulant laxatives have a strong defecation effect; however, they are not suited for uses over a long period, because continued use results in tolerance. Furthermore, known methods for treating IBS include methods using anticholinergic agents to decrease abnormal intestinal spasms, methods using dietary fibers or the like to aid the movement of content by the effect of adjusting the stool water content and by a gelling effect, and methods using antianxiety agents to relieve the stress symptoms. However, many of the anticholinergic agents are designated as dangerous agents (e.g., Trancolon). Furthermore, polycarbophil calcium preparations which adjust the water content through gelling effect are contraindicated in patients with an acute abdominal disease, hypercalcemia, renal failure, nephrolithiasis, and such. Thus, the development of highly safe, novel preventive or therapeutic agents for functional gastrointestinal disorders has been expected.

Fermentation products by *Propionibacterium freudenreichii* are known as propionic acid bacteria fermentation products, and have been reported to be effective in the proliferation of various bifidobacteria, in the improvement of inflammatory bowel diseases, and such (Patent Document 1). Furthermore, 1,4-dihydroxy-2-naphthoic acid (DHNA), a component of fermentation products of propionic acid bacteria, has also been found to have the effect of promoting bifidobacterial proliferation (Patent Document 2), the effect of preventing and treating metabolic bone diseases (Patent Document 3), and the effect of alleviating the symptoms of abdominal discomfort of milk intolerance after milk ingestion (Patent Document 4).

[Patent Document 1] International publication WO 2005/099725 pamphlet.
[Patent Document 2] Japanese Patent Application Kokai Publication No. (JP-A) H08-98677 (unexamined, published Japanese patent application).
[Patent Document 3] International publication WO 01/28547 pamphlet.
[Patent Document 4] International publication WO 03/016544 pamphlet.
[Non-Patent Document 1] "Saishin Naikagaku Taikei, Progress 8, Shoukakan Shikkan (Latest Internal Medicine Outline, Progress 8, Gastrointestinal Diseases)", Eds., Imura H. et al., pp. 51, 1997, Nakayama Shoten.

DISCLOSURE OF THE INVENTION

Problems to be Solved by the Invention

An objective of the present invention is to provide highly safe agents for preventing and/or treating functional gastrointestinal disorders.

Means for Solving the Problems

The present inventors conducted dedicated studies, and as a result, discovered that propionic acid bacteria fermentation products have a preventive/therapeutic effect on functional gastrointestinal disorders in in vitro studies and studies using patients with irritable bowel syndrome, and completed the present invention.

Specifically, it was discovered in the in vitro studies that the products have an effect of increasing the intestinal contraction frequency, without changing the intestinal contractile force, in a distal colon-specific manner. In addition, effects of improving defecation condition, general abdominal condition, and health-related QOL in patients with irritable bowel syndrome were discovered. Furthermore, it is possible to ingest a large amount of propionic acid bacteria fermentation product. Therefore, propionic acid bacteria fermentation products are expected to have a preventive/therapeutic effect on functional gastrointestinal disorders safely.

Therefore, the present invention comprises the following:

[1] an agent for preventing and/or treating a functional gastrointestinal disorder, which comprises as an active ingredient a propionic acid bacterium fermentation product and/or processed product thereof;

[2] the agent of [1] for preventing and/or treating a functional gastrointestinal disorder, wherein the propionic acid bacterium is a bacterium belonging to the genus *Propionibacterium*;

[3] the agent of [2] for preventing and/or treating a functional gastrointestinal disorder, wherein the bacterium belonging to the genus *Propionibacterium* is *Propionibacterium freudenreichii*;

[4] the agent of [3] for preventing and/or treating a functional gastrointestinal disorder, wherein *Propionibacterium freudenreichii* is *Propionibacterium freudenreichii* ET-3 (FERM BP-8115);

[5] the agent of any one of [1] to [4] for preventing and/or treating a functional gastrointestinal disorder, wherein the propionic acid bacterium fermentation product is a propionic acid bacterium whey fermentation product;

[6] the agent of any one of [1] to [5] for preventing and/or treating a functional gastrointestinal disorder, wherein the functional gastrointestinal disorder is one or a combination of a plurality from the group consisting of irritable bowel syndrome and functional constipation;

[7] a food for preventing and/or treating a functional gastrointestinal disorder, which comprises an agent of any one of [1] to [6] for preventing and/or treating a functional gastrointestinal disorder;

[8] use of a propionic acid bacterium fermentation product in the manufacture of an agent of any one of [1] to [6] for preventing and/or treating a functional gastrointestinal disorder;

[9] use of a propionic acid bacterium fermentation product in the manufacture of the food of [7] for preventing and/or treating a functional gastrointestinal disorder; and

[10] a method for preventing and/or treating a functional gastrointestinal disorder, which comprises administering a propionic acid bacterium fermentation product and/or a processed product thereof.

Effects of the Invention

The agents of the present invention for preventing and/or treating functional gastrointestinal disorders enable safe prevention and/or treatment of functional gastrointestinal disorders, especially of irritable bowel syndrome, spastic constipation, and functional constipation.

BRIEF DESCRIPTION OF THE DRAWINGS

FIG. 3 is a questionnaire on general abdominal conditions. This was used in Example 4.

BEST MODE FOR CARRYING OUT THE INVENTION

Figure 1:
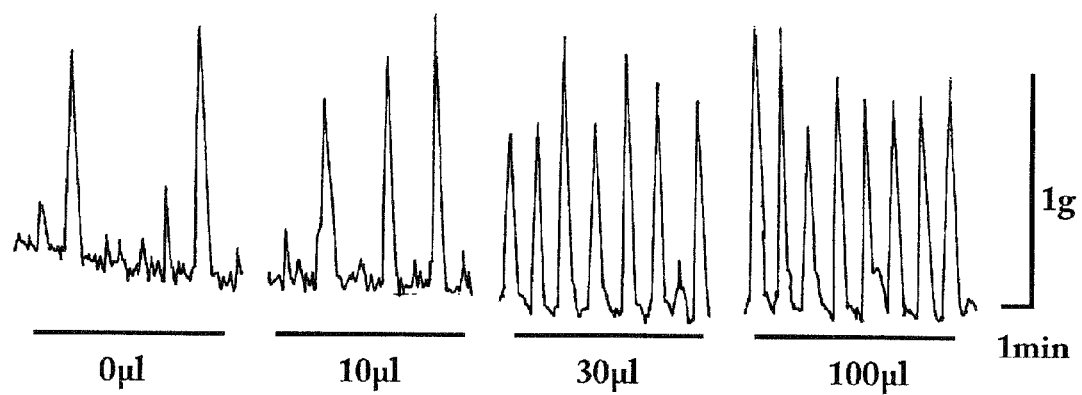
FIG. 1 shows representative charts obtained when measuring the effect of propionic acid bacteria whey fermentation product on the intestinal smooth muscle. An example of measured charts observed when propionibacterial whey fermentation product was added to the distal colon in Example 1 is shown.

Hereinbelow, the present invention will be described more specifically, but is not to be construed as being limited to the preferred embodiments described below. Any change may be made within the scope of the present invention.

The propionic acid bacteria fermentation product, which is an active ingredient of the agents of the present invention for preventing and/or treating functional gastrointestinal disorders, can be produced according to known production methods, such as that described in International Publication No. WO 03/016544 pamphlet. Herein, the "propionic acid bacteria fermentation product" refers to the culture per se obtained through fermentation by a propionic acid bacterium. The agents of the present invention for preventing and/or treating functional gastrointestinal disorders comprise propionic acid bacteria fermentation products as well as processed products thereof, for example, culture filtrates and culture supernatants obtained by removing bacteria from the aforementioned culture (propionic acid bacteria fermentation product) by filtration/centrifugation, membrane separation, or such; concentrates obtained by concentrating the aforementioned culture filtrate/culture supernatant, propionic acid bacteria fermentation product, or such using an evaporator or the like; pastes; dilutions; and dried materials (freeze-dried, heat-dried, reduced-pressure dried, or such); and bactericidal treatment products or sterilization products of these. In the present invention, one or a combination of a number of the aforementioned treatment steps, such as the bacteria-removing treatment such as filtration, centrifugation, and membrane separation, precipitation, concentration, paste formation, dilution, drying, bactericidal treatment, and sterilization, may be used to prepare the processed products.

Media used to produce propionic acid bacteria fermentation products in general contain nutrient sources that enable the growth of microorganisms. It is possible to add, as nutrient source, whey, casein, skimmed milk, whey protein concentrate (WPC), whey protein isolates (WPI), yeast extract, soybean extract, peptone such as trypticase, glucose, sugars such as lactose, and minerals such as whey minerals, or food containing these abundantly. Alternatively, enzyme-treated products of these may be added. In particular, whey or enzyme digestion products thereof are preferably used; however, the nutrient sources are not limited to these examples. In the present invention, propionic acid bacteria fermentation products prepared using, as nutrient source, whey or materials derived from whey such as WPC and WPI are referred to hereinafter as "propionic acid bacteria whey fermentation products".

Enzymes that are used to enzymatically digest the above-described nutrient sources include one or a combination of a number of proteases and peptidases. The proteases and peptidases to be used are not particularly limited; examples of food-grade proteases include endo-type proteases, exo-type proteases, exo-type peptidase/endo-type protease conjugate enzymes, and protease/peptidase conjugate enzymes. Endo-type proteases include, for example, chymosin (EC 3.4.23.4; Maxiren, derived from modified yeast *Kluyveromyces lactis*; GIST-BROCADES N.V.), AlcalaseR (derived from *Bacillus licheniformis*; Novo), Esperase (derived from *B. lentus*; Novo), NeutraseR (derived from *B. subtilis*; Novo), Protamex (derived from bacteria; Novo), and PTN6.0S (porcine pancreatic trypsin; Novo). Exo-type peptidase/endo-type protease conjugate enzymes include, for example, Flavourzyme (derived from *Aspergillus oryzae*; Novo). Furthermore, endo-type proteases include, for example, trypsin (CAS No. 9002-07-7, EC 3.4.21.4; derived from bovine pancreas; Product No. T8802, SIGMA), pepsin (CAS No. 9001-75-6, EC 3.4.4.1; derived from porcine gastric mucosa; SIGMA), chymotrypsin (Novo and Boehringer), protease N "Amano" G (derived from *Bacillus subtilis*; AMANO ENZYME), Bioprase (derived from *Bacillus subtilis*; Nagase & Co. Ltd.), and papain W-40 (AMANO ENZYME). Exo-type proteases include pancreatic carboxypeptidase and aminopeptidase from the brush border of the small intestine. Moreover, the protease/peptidase conjugate enzymes that can be used include, for example, protease A "Amano" G (derived from *Aspergillus oryzae*; AMANO ENZYME) and Umamizyme G (peptidase and protease, derived from *Aspergillus oryzae*; AMANO ENZYME). The enzyme origin is not limited to those described above, and the enzymes may be derived from any of animal, plant, or microorganism. However, those derived from *Aspergillus oryzae* are preferred. These enzymes do not refer to those limited by trade names, origins, manufacturers, and the like. One type of enzyme or a combination of two types of more may be used to carry out the present invention. Preferred examples include protease A "Amano" G (derived from *Aspergillus oryzae*; AMANO ENZYME); however, the enzyme is not limited to this example. When the above-described enzymes are used in combination, each enzymatic reaction may be conducted separately or simultaneously.

When digesting the aforementioned nutrient sources enzymatically, the nutrient source which is the raw material is dispersed and dissolved in water or warm water, and enzymes are added thereto. The pH at the start of enzymatic digestion, the time of enzymatic digestion, and the temperature of the enzyme reaction are not particularly limited as long as the product of the present invention can be obtained. For example, the pH at the start of enzymatic digestion can be 3.0 to 7.5, preferably 4.5 to 7.0, and more preferably 6.0 to 7.0. The time of enzymatic digestion may be 0.5 to 300 hours, preferably 1 to 20 hours, and more preferably 1 to 5 hours. The temperature of the enzyme reaction may be 20° C. to 57° C., preferably 30° C. to 52° C., and more preferably 40° C. to 52° C.

Without limitation, a preferred example for preparing a medium for producing a propionic acid bacterium fermentation product is the following method: whey powder (10 w/w %) and protease Amano A "Amano" G (0.07 w/w %; AMANO ENZYME) are dissolved in water; after two hours of enzyme digestion at 47° C. (pH 6.6), the enzyme is inactivated by heating at 85° C. for 10 minutes; then, beer yeast extract (0.10 w/w %; ASAHI BREWERIES) and ammonium sulfate (0.27 w/w %) are added thereto, and the pH is adjusted to 6.7; and sterilization is carried out at 121° C. for seven minutes.

Propionic acid bacteria that are used to produce the propionic acid bacteria fermentation products include those of the genera *Propionibacterium, Propionicimonas, Propioniferax, Propionimicrobium*, and *Propionivibrio*. Preferred bacteria are those belonging to the genus *Propionibacterium*, but are not limited thereto. Bacteria of the genus *Propionibacterium* include, for example, bacteria for cheese, such as *Propionibacterium freudenreichii, Propionibacterium thoenii, Propionibacterium acidipropionici*, and *Propionibacterium jensenii; Propionibacterium avidum; Propionibacterium acnes; Propionibacterium lymphophilum; Propionibacterium granulosam; Propionibacterium arabinosum; Propionibacterium cyclohexanicum; Propionibacterium innocuum; Propionibacterium intermediu; Propionibacterium pentosaceum; Propionibacterium peterssonii; Propionibacterium propionicum*; and *Propionibacterium zeae*. Among these, *Propionibacterium freudenreichii* (hereinafter also referred to as *P. freudenreichii*) is preferred, more preferably *Propionibacterium freudenreichii* IFO 12424 and *Propionibacterium freudenreichii* ATCC 6207 are preferred; in particular, *Propionibacterium freudenreichii* ET-3 (FERM BP-8115) is preferred.

The present inventors have deposited the *Propionibacterium freudenreichii* ET-3 strain to the International Patent Organism Depositary, National Institute of Advanced Industrial Science and Technology (AIST), Independent Administrative Institution. Information specifying the deposition is as follows:

(1) Name of depositary institution: International Patent Organism Depositary, National Institute of Advanced Industrial Science and Technology (AIST), Independent Administrative Institution
(2) Address: Tsukuba Central 6, 1-1-1 Higashi, Tsukuba, Ibaraki, 305-8566
(3) Accession Number: FERM BP-8115
(4) Identification reference: ET-3
(5) Date of original deposit: Aug. 9, 2001
(6) Date of transfer to deposit under the Budapest Treaty: Jul. 11, 2002

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depositary be unable to furnish a sample when requested, due to the condition of the deposit. All restrictions on the availability to the public of the subject culture deposit will be irrevocably removed upon the granting of a patent disclosing it.

The above-described *Propionibacterium freudenreichii* ET-3 was isolated from Emmental cheese. It is a gram-positive short *bacillus*, and is negative in nitrate-reducing ability, negative in indole-producing ability, negative in hydrogen sulfide-producing ability, and positive in lactose-fermenting ability. It also has the ability to produce DHNA.

Bacterial strains whose bacterial strain name is labeled "ATCC" are standard strains obtained from the American Type Culture Collection, while those with bacterial strain names labeled "IFO" are standard strains obtained from the Institute for Fermentation.

Next, these propionic acid bacteria are cultured using the above-described media. Known aerobic or anaerobic culture methods can be used as culture method; however, aerobic or anaerobic culture methods using liquid media are preferred. The pH at the start of fermentation and the time and temperature of fermentation are not particularly limited as long as the agents of the present invention for preventing and/or treating functional gastrointestinal disorders can be obtained. However, the pH at the start of fermentation may be 3.0 to 7.5, preferably 5.0 to 7.5, and more preferably 5.5 to 7.0. The time for fermentation may be 0.5 to 200 hours, preferably 50 to 100 hours, and more preferably 60 to 99 hours. The fermentation temperature may be 20° C. to 50° C., preferably 25° C. to 45° C., and more preferably 30° C. to 40° C. Culture media thus obtained may be used immediately after culture. However, the culture media are preferably used after cooling (3° C. to 20° C., preferably about 10° C.) and storing for about two to four weeks. Without limitation, an example of a preferred method is the following method: the pH of a culture medium is adjusted to 6.8, and then the medium is sterilized at 121° C. for seven minutes; this medium is inoculated at 0.01 to 2.5% with an activation culture medium of *P. freudenreichii* ET-3 (FERM BP-8115 strain); anaerobic culture is carried out at 32° C. to 37° C. for 72 to 99 hours under nitrogen atmosphere; and the obtained culture solution is used as propionic acid bacterium fermentation product.

For example, in the case a culture medium is prepared by digestion of an approximately 10 w/w % whey aqueous solution with protease A "Amano" G (at 40° C. to 52° C. and pH 6.0 to 7.0 for 1 to 5 hours) and addition of beer yeast extract and ammonium sulfate, and a propionic acid bacteria whey fermentation product is produced by inoculation at 0.01 to 2.5% of an activation culture solution of the aforementioned *Propionibacterium freudenreichii* ET-3 and anaerobic culture under nitrogen atmosphere at 32° C. to 37° C. for 72 to 99 hours, the bacterial concentration of *Propionibacterium freudenreichii* ET-3 is about 0.5 to 50×cfu/mL; the DHNA content is about 5 to 500 µg/mL; and the solid content is about 5 to 15 w/w %.

Furthermore, the agent of the present invention for preventing and/or treating functional gastrointestinal disorders can be obtained as the aforementioned propionic acid bacteria fermentation product or processed product thereof as is, or as a soluble or insoluble fraction after dilution with a solvent. Solvents include water and commonly used solvents, for example, alcohols, hydrocarbons, organic acids, organic bases, inorganic acids, inorganic bases, and supercritical fluids, which can be used alone or in combination of a plurality.

The agents for preventing and/or treating functional gastrointestinal disorders thus obtained may be used as is. Alternatively, they can be used as solution obtained after this solution is concentrated or diluted by known methods as required. Furthermore, they can be used after this concentrated solution is made into a dried material by known methods.

The agents of the present invention for preventing and/or treating functional gastrointestinal disorders are useful as compositions effective in the prevention and/or treatment of functional gastrointestinal disorders. This has been confirmed by the Magnus method using rat intestinal smooth muscles as well as clinical studies conducted on IBS patients.

Irritable bowel syndrome (IBS) is caused by functional abnormalities of the lower digestive tract. The pathophysiology of IBS is known to be motility abnormalities of the intestine, mainly, of the colon. The observed symptoms include abdominal pain, abdominal discomfort (characterized by a relief by defecation), defecation abnormalities (diarrhea, constipation, and combination of diarrhea and constipation), abnormal stool form (inclusion of mucus and abnormal hardness), and sense of abdominal bloating. The time for intestinal passage is shortened in the diarrhea type, while the time is prolonged in the constipation type. Although the area and contractility differ, an abnormal intestinal motility state is observed in both cases. It is said that, as compared to healthy individuals, IBS patients show abnormal reactions to stress, stimuli such as diet, and cholinergic agents. It is also said that a reduction in the perception threshold to balloon stimuli of rectum or ileocecum occurs ("Saishin Naikagaku Taikei, Progress 8, Shoukakan Shikkan (Latest Internal Medicine Outline, Progress 8, Gastrointestinal Diseases)", Eds., Imura H. et al., pp. 51, 1997, Nakayama Shoten).

The colon is an organ undertaking functions such as absorption of water content and electrolytes from contents, maintenance of enteric bacteria, and defecation. In order to maintain these functions, it is important to move the contents from the small intestine at an appropriate speed. For example, when the upper colon peristalsis is enhanced in IBS, absorption from contents of water content and such becomes insufficient, and as a result, diarrhea symptoms are manifested. Alternatively, when the intestinal movement becomes irregular, propulsion of contents is affected, so that constipation symptoms are manifested.

The following three types and such exist as functional constipation:

1. Habitual constipation (rectal constipation): constipation occurring, for example, in persons leaving in the morning without time to defecate and caused by a decrease in the function of feeling a desire to defecate (rectal sensitivity) due to continued endurance of the urge to defecate.
2. Atonic constipation: constipation often occurring in middle-aged or older women and caused by a dulling of colon movement. Since the passage of the intestine content is retarded, water content absorption is increased.
3. Spastic constipation: constipation in which colonic spasms occur because of stress, the spastic part constricts such that stool cannot pass smoothly in the colon, water content absorption becomes excessive, resulting in hard stool like rabbit feces.

Known conventional laxative agents appropriate for habitual and atonic constipations include those that expand the stool with moisture to improve the stool property and induce a desire to defecate (bulk-forming laxatives: dietary fiber preparations, saline laxatives, sugar laxatives, etc) and those that directly promote the intestinal movement, in particular, the intestinal contractile force (stimulant laxative: rhubarb, sennosides, sodium picosulfate, etc). Stimulant laxatives have a strong defecation effect; however, they are not suited for uses over a long period, because continued use results in tolerance. Meanwhile, stress relieving is effective for spastic constipation. In these cases, even though the aforementioned laxative agents are taken, because the stool at the exit has become hard, it may often only lead to abdominal pain.

In the constipation type irritable bowel syndrome, there is no organic abnormality, and since aberrantly high sensitivity to stress or the like is shown, an increase in the tension and a decrease in peristalsis are observed in the whole colon, and spastic constipation occurs (Mizutani, M. and Nakayama, S., "Daicho no Undousei to Haibenkinou oyobi Benpi no Byotaiseiri, Rinshouseiri series 6, Cho (Colon motility, defecation functions, and pathophysiology of constipation, Clinical Physiology series 6, Intestine", Eds., Asakura H. et al., pp. 180-184, Nankodo, Tokyo, 1990). Accordingly, the constant maintenance of normal colonico peristaltic movement is thought to be important for relief from constipation.

Conventionally known methods for treating irritable bowel syndrome (constipation type and diarrhea type) include methods in which abnormal intestinal spasms are relieved by anticholinergic agents (Scopolia extract, mepenzolate bromide, and such) and methods in which the content movement is aided by the water content-adjusting effect and gelling effect of dietary fibers (polycarbophil calcium, etc) or such. Moreover, trimebutine maleate which is used as a therapeutic agent for irritable bowel syndrome directly acts on smooth muscles of the digestive tract and modulates enterokinesis by acting in a suppressive manner in a state of increased motility of the digestive tract and by acting in a promoting manner in a state of decreased motility.

Meanwhile, the in vitro tests described below have revealed that the propionic acid bacteria fermentation products of the present invention increase the contraction frequency of the distal colon without increasing the contractile force. Furthermore, the propionic acid bacteria fermentation products of the present invention showed an effect of improving patients' symptoms (defecation condition and general abdominal condition) and health-related QOL in the tests using patients with constipation-type irritable bowel syndrome described below. Thus, they can be regarded as materials suitable for constipation-type irritable bowel syndrome including spastic constipation.

Among disorders showing diarrhea symptom, irritable bowel syndrome is the most frequent, and results from chill in the abdomen or excessive drinking of beverage in the summer, a series of worries or stresses, and the like. Particularly in a high-stress society such as today's society, it is a disease from which many people suffer. A possible mechanism thereof includes enhanced secretion of water/electrolytes, impaired water content absorption from the intestine, abnormalities in intestinal motility, and such. Characteristically, the body weight is unaltered because digestion and absorption of nutrients are maintained. Abnormalities in intestinal motility include those resulting from enhanced intestinal motility and those resulting from decreased intestinal motility.

With regard to the small intestine, retardation of the passage of the small intestine content results in proliferation of bacteria in the small intestine and induction of deconjugation of bile acid, leading to impaired lipid or water absorption, so that diarrhea may occur.

On the other hand, regarding the colon, Munakata et al. developed a method of endoscopic retrograde colon intubation. Using this method, they inserted two Teflon™ tubes into two sites, the ascending colon and the sigmoid colon, introduced microchips, and obtained intracolonic pressure curves to observe colonic movements (Munakata A., Kawakami K., et al., "Kaichobu Chubu Ryuchihou no Kouan to Oyo (Devisal and application of ileal tube indwelling method)", Gastroenterol. Endsc., 21, 448-457 (1979)). In patients with diarrhea-type irritable bowel syndrome, the inner pressure at rest is lower in the sigmoid colon at the distal side than in the ascending colon at the proximal side, and the intestinal pressure gradient becomes lower toward the anal side; therefore, the intestinal content is easily pushed out to the rectum and beyond. This phenomenon is not improved even by administration of prostigmine, an anticholinergic agent (Kawakami K., "Kabinsei Choshokogun: Jiristushinkei no Kiso to Rinshou (Irritable Bowel Syndrome: Basic and Clinical Aspects of Autonomic Nerves)" Eds., Goto Y. et al., pp. 276-303, Iyaku Journal (Medicine and Drug Journal) Co., Ltd., Osaka/Tokyo, 1982). Therefore, increasing the inner pressure of the sigmoid colon is expected to be effective to treat or prevent diarrhea-type irritable bowel syndrome.

Furthermore, studies on the inner pressure of sigmoid colon suggest that reduced motor functions is involved in diarrhea (The Merck Manual 17th Ed., Japanese Edition, Section 3, Gastrointestinal diseases, Functional Bowel Disorders, Irritable Bowel Syndrome (IBS), http://merckmanual.banyu.co.jp/cgi-bin/disphtml.cgi?url=03/s032.html (Jan. 15, 2008), homepage of BANYU PHARMACEUTICAL CO., LTD.). A possible effective method for increasing a reduced inner pressure of the sigmoid colon is to increase the contraction frequency of the sigmoid colon. The propionic acid bacteria fermentation products of the present invention have the activity of increasing the contraction frequency of the distal colon. This indicates that the propionic acid bacteria fermentation products of the present invention have an effect of enhancing motility on sigmoid colon with decreased function and increase the inner pressure, so that the pressure of the proximal colon is increased in a retrograde manner and the pressure gradient is improved. Hence, the propionic acid bacteria fermentation products of the present invention are considered to be effective to diarrhea-type irritable bowel syndrome as well.

Therefore, it is not just the suppression of enhanced intestinal motility that results in suppression of diarrhea, and the maintenance of an appropriate pressure gradient can be an important factor as well.

The agents of the present invention for preventing and/or treating functional gastrointestinal disorders increased the contraction frequency of intestinal smooth muscles of distal colon without increasing their contractile force in the in vitro tests described below. The activity of increasing the contraction frequency was not observed with the medium before inoculation of propionic acid bacteria. Thus, fermentation by propionic acid bacteria was demonstrated to be important. Meanwhile, the same tests were conducted with the proximal colon and middle colon; however, there was no influence on both the contractile force and contraction frequency of the intestinal smooth muscles. Based on this finding, the agents of the present invention for preventing and/or treating functional gastrointestinal disorders are expected to have an effect of moving the colonic content to the anus while sufficiently maintaining water content absorption in the proximal colon and middle colon, eliminating the content from the distal colon, and increasing the internal pressure even to a small extent as compared the proximal colon and middle colon. In other words, they are thought to be useful materials against diarrhea-type irritable bowel syndrome as well.

The agents of the present invention for preventing and/or treating functional gastrointestinal disorders can be used as compositions effective to prevent and/or treat functional gastrointestinal disorders applicable to functional gastrointestinal disorders, in particular, irritable bowel syndrome (constipation type, diarrhea type, and combination type), spastic constipation, functional constipation, and the like. Furthermore, the agents for preventing and/or treating functional gastrointestinal disorders can be prepared efficiently, with few steps. Thus, there is the advantage that the agents for preventing and/or treating functional gastrointestinal disorders, which are superior in safety and which can be added to food and beverages as well as pharmaceuticals, can be easily provided.

The amount of an agent of the present invention for preventing and/or treating functional gastrointestinal disorders that is mixed into a pharmaceutical, food or beverage is not particularly limited, since it varies depending on the form, dosage form, symptom, body weight, use, and such. However, the agents can be mixed, for example, at a content of 0.001 to 100% (w/w), preferably 0.01 to 100% (w/w), and more preferably 0.1 to 100% (w/w) when converted to the dry weight of propionic acid bacteria fermentation product.

The daily dose of a pharmaceutical or food or beverage of an agent of the present invention for preventing and/or treating functional gastrointestinal disorders is not particularly limited, since the dose varies depending on the age, symptom, body weight, use, and such. However, they can be taken, for example, at 0.1 to 10000 mg/kg body weight, preferably 1 to 400 mg/kg body weight, and more preferably 5 to 40 mg/kg body weight when converted to the dry weight of propionic acid bacteria fermentation product.

Furthermore, they may be used in combination with conventionally known pharmaceuticals or food having an effect of preventing and/or treating functional gastrointestinal disorders. Specifically, examples include, without limitation, anticholinergic agents and food containing dietary fibers.

The agents of the present invention for preventing and/or treating functional gastrointestinal disorders can be used in both the pharmaceutical form and the food or beverage form. For example, various types of inflammation are expected to be treated and/or prevented by direct administration as pharmaceutical, or by direct ingestion as special use food such as food for specified health use, food with nutritive function, or supplement. Further, regardless of the form such as liquid, paste, solid, and powder, they can be added to various types of food (milk, beverages, fermented milk, yogurt, cheese, bread, biscuits, crackers, pizza crusts, powdered milk formulation, fluid diet, food for sick people, nutritional food, frozen food, processed food, other commercially available food, and the like), and this can be ingested.

Water, proteins, carbohydrates, lipids, vitamins, minerals, organic acids, organic bases, fruit juices, flavoring, and such can be used as main component for the food comprising an agent of the present invention for preventing and/or treating functional gastrointestinal disorders. Proteins include, for example, animal and plant proteins such as whole milk powder, skimmed milk, partially skimmed milk, casein, whey powder, whey proteins, whey protein concentrates, whey protein isolates, α-casein, β-casein, κ-casein, β-lactoglobulin, α-lactalbumin, lactoferrin, soybean protein, hen egg protein, and meat protein, and digestion products thereof; and various milk-derived components such as butter, whey minerals, cream, whey, non-protein nitrogen, sialic acid, phospholipids, and lactose. They may include peptides and amino acids such as casein phosphopeptides, arginine, and lysine. Carbohydrates include, for example, sugars, processed starches (dextrin, soluble starch, British starch, oxidized starch, starch ester, starch ether, and the like) and dietary fibers. Lipids include, for example, animal oils such as lard, fish oils, as well as separated oils, hydrogenated oils, and transesterified oils thereof; and vegetable oils such as palm oil, safflower oil, corn oil, rapeseed oil, and coconut oil, as well as separated oils, hydrogenated oils, and transesterified oils thereof. Vitamins include, for example, vitamin A, carotenes, vitamin B group, vitamin C, vitamin D group, vitamin E, vitamin K group, vitamin P, vitamin Q, niacin, nicotinic acid, pantothenic acid, biotin, inositol, choline, and folic acid. Minerals include, for example, calcium, potassium, magnesium, sodium, copper, iron, manganese, zinc, and selenium. Organic acids include, for example, malic acid, citric acid, lactic acid, tartaric acid, and erythorbic acid. Two or more of these elements may be used in combination, and synthetic products and/or food comprising these abundantly may also be used. The food form may be solid or liquid form. Alternatively, it may be a gel form or the like.

When used as pharmaceuticals or supplements, the agents of the present invention for preventing and/or treating functional gastrointestinal disorders can be administered in various forms. Examples of form include oral administration using tablets, capsules, granules, powders, syrups, and such. These various preparations can be formulated following conventional methods by using, as main agent, known adjuvants that can be commonly used in the technical field of pharmaceutical formulation, such as excipients, binders, disintegrants, lubricants, smell corrigents, solubilizing agents, suspending agents, and coating agents. Furthermore, an appropriate amount of calcium may also be contained. Moreover, appropriate amounts of vitamins, minerals, organic acids, sugars., amino acids, peptides, and the like may also be added.

All prior art references cited herein are incorporated by reference into this description.

EXAMPLES

Hereinbelow, the present invention will be specifically described with reference to Examples, but it is not to be construed as being limited thereto.

Example 1

Preparation of Propionic Acid Bacterium Whey Fermentation Product

Preparation of Culture Medium

Whey powder (10 w/w %) and protease A "Amano" G (0.07 w/w %, AMANO ENZYME) were dissolved in water and enzyme digestion was carried out at 47° C. (pH 6.6) for two hours. Then, the enzyme was inactivated by heating at 85° C. for ten minutes. Next, beer yeast extract (0.10 w/w %; ASAHI BREWERIES) and ammonium sulfate (0.27 w/w %) were added, the pH was adjusted to 6.7, then the solution was sterilized at 121° C. for seven minutes.

Culture of Propionic Acid Bacteria

The prepared medium was inoculated at 2% with an activation culture solution of *P. freudenreichii* ET-3 (FERM BP-8115 strain) and anaerobically cultured under nitrogen atmosphere at 37° C. for 72 hours to obtain a propionic acid bacterium fermentation product of whey (DHNA content, 0.01 w/w %). The same medium as that described above was used for the activation culture solution.

Example 2

Effect of Propionic Acid Bacteria Whey Fermentation Product on Intestinal Smooth Muscles Preparation of Colon Specimens Six-week-old SD type male rats were reared and habituated for one week, then sacrificed to excise the colon. Then, about 1 cm of the longitudinal muscle of the colon was isolated from the distal colon (a portion at about 2 to 3 cm to the appendix side from the anus), and was cut in the longitudinal layer direction with a width of 3 mm (hereinafter, this is also referred to as colon specimen). Each colon specimen was hung with resting tension of 1 g in a Magnus tube filled with Krebs buffer under the condition described below, and a mixed gas of 95% oxygen and 5% carbon dioxide was passed thereto. Then, the colon specimens were equilibrated for about one hour while changing the Krebs buffer every 15 minutes.

Composition of Krebs Buffer:

Distilled water was added to 6.92 g of NaCl, 0.35 g of KCl, 0.29 g of $MgSO_4 \cdot 7H_2O$, 0.16 g of $KH_2PO_4$, 2.1 g of glucose, 0.28 g of $CaCl_2$ and 2.1 g of $NaHCO_3$ to obtain 1 L.

Temperature of Krebs buffer in the Magnus tube: 32° C.

Volume of Krebs buffer introduced into the Magnus tube: 10 mL.

Preparation of Test Substances

The whey fermentation product by propionic acid bacteria prepared in Example 1 was sterilized by γ irradiation. Distilled water was added to the freeze-dried product to prepare a 10 w/v % (conversion from the freeze-dried product) aqueous solution of propionic acid bacteria whey fermentation product. Furthermore, distilled water was added to the freeze-dried product of the medium before inoculation of the propionic acid bacterium prepared in Example 1 (hereinafter also referred to as "unfermented product") to prepare a 10 w/v % (conversion from the freeze-dried product) aqueous solution of unfermented product. These aqueous solutions of test substances were used in the assessment test described below. Meanwhile, distilled water was used as control.

Assessment Test on Propionic Acid Bacteria Whey Fermentation Products

After changing the Krebs buffer, 10 μL, 30 μL, and 100 μL of an aqueous solution of propionic acid bacteria whey fermentation product, an aqueous solution of unfermented product, or distilled water were added to each of the Magnus tube (at final concentrations of 0.01, 0.03, and 0.10 w/v %), and the measurement of tension and observation of muscle conditions were carried out for 15 minutes. Tension measurement charts were recorded using a recorder adjusted such that a 5 cm displacement occurs per tension of 1 g on the measurement charts. The resulting measurement charts were used to observe peaks of tension associated with muscle contraction. The contraction frequency (times/minute) was calculated from the number of peaks (times) that appeared per unit time (minute), the contractile force (g) was calculated from the peak height (cm), and numerical values were used for evaluation.

Results

The determined contraction frequency and contractile force of each part of the colon are shown in Table 1.

TABLE 1

| | ADDED SUBSTANCE | AMOUNT OF TEST SUBSTANCE AQUEOUS SOLUTION ADDED (μL) | CONTRACTILE FORCE (g) | CONTRACTION FREQUENCY (TIMES/MINUTE) |
|---|---|---|---|---|
| DISTAL COLON mean ± SD | DISTILLED WATER n = 4 | 0 | 0.48 ± 0.15 | 1.17 ± 0.53 |
| | | 10 | 0.48 ± 0.14 | 1.13 ± 0.63 |
| | | 30 | 0.49 ± 0.11 | 0.75 ± 0.48 |
| | | 100 | 0.48 ± 0.08 | 0.79 ± 0.25 |
| | UNFERMENTED PRODUCT n = 4 | 0 | 0.40 ± 0.14 | 0.75 ± 0.29 |
| | | 10 | 0.34 ± 0.10 | 0.88 ± 0.16 |
| | | 30 | 0.39 ± 0.11 | 0.88 ± 0.16 |
| | | 100 | 0.46 ± 0.20 | 0.75 ± 0.35 |
| | PROPIONIC ACID BACTERIA FERMENTATION PRODUCT n = 4 | 0 | 0.46 ± 0.14 | 0.88 ± 0.32 |
| | | 10 | 0.38 ± 0.10 | 1.29 ± 0.34 |
| | | 30 | 0.44 ± 0.22 | 1.75 ± 1.83 + |
| | | 100 | 0.48 ± 0.14 | 1.83 ± 0.14 ++, * |

*: $p < 0.05$ vs before addition of test substance aqueous solution (0) (paired t-test)
+, ++: $p < 0.05$, $0.01$ vs unfermented product (Student's t-test)

In this table, * indicates that there is a significant difference of $p<0.05$ (paired t-test) versus before addition of the test substance to the colon specimen (i.e. volume of added test substance aqueous solution is 0 μL). + and ++ indicate that there is a significant difference of $p<0.05$ and $p<0.01$ (Student's t-test) versus unfermented product, respectively.

The contraction frequency of the distal colon increased by addition of the propionic acid bacteria whey fermentation product in a dose dependent manner. When 100 μL of the aqueous solution of propionic acid bacteria whey fermentation product was added, the contraction frequency showed a significantly higher value ($p<0.05$, paired t-test) as compared to before addition. Even when compared to the unfermented product, the contraction frequency significantly increased upon addition of 30 μL or 100 μL of the aqueous solution of propionic acid bacteria whey fermentation product, with $p<0.05$ and $p<0.01$ (Student's t-test), respectively. In contrast, with the unfermented product not inoculated with the propionic acid bacterium, no effect of increasing the contraction frequency as compared to distilled water or before addition was observed.

The contractile force was not altered by addition of either of the test substances. In other words, the propionic acid bacteria whey fermentation product has neither a contractile force-increasing effect nor a contractile force-suppressing effect. Thus, the propionic acid bacteria whey fermentation product was found to have an effect of increasing contraction frequency, but not to have any effect of increasing contractile force.

Example 3

Effect of Propionic Acid Bacteria Whey Fermentation Product on Intestinal Smooth Muscles in Various Areas Preparation of Colon Specimens Six-week-old SD type male rats were reared and habituated for one week, then sacrificed to excise the colon. Then, about 1 cm each of the longitudinal muscle of the colon was isolated from the proximal colon (a portion at about 1 cm to the anal side from the appendix side), middle colon (the middle portion in view of the whole colon), and the distal colon (a portion at about 2 to 3 cm to the appendix side from the anus), and cut into two pieces in the longitudinal layer direction (hereinafter these are also referred to as colon specimens). Each colon specimen was hung with resting tension of 1 g in a Magnus tube filled with Krebs buffer under the condition described below, and a mixed gas of 95% oxygen and 5% carbon dioxide was passed thereto. Then, the colon specimens were equilibrated for about one hour while changing the Krebs buffer every 15 minutes.

Composition of Krebs Buffer:

Distilled water was added to 6.92 g of NaCl, 0.35 g of KCl, 0.29 g of $MgSO_4.7H_2O$, 0.16 g of $KH_2PO_4$, 2.1 g of glucose, 0.28 g of $CaCl_2$, and 2.1 g of $NaHCO_3$ to obtain 1 L.

Temperature of Krebs buffer in the Magnus tube: 32° C.
Volume of Krebs buffer introduced into the Magnus tube: 10 mL.

Preparation of Test Substances

The propionic acid bacteria fermentation product of whey prepared in Example 1 was sterilized by γ irradiation. Distilled water was added to the freeze-dried product to prepare a 10 w/v % (conversion from the freeze-dried product) aqueous solution of propionic acid bacteria whey fermentation product. This was used as test substance aqueous solution in the assessment test described below. Meanwhile, distilled water was used as control.

Assessment Test on Propionic Acid Bacteria Whey Fermentation Product

After changing the Krebs buffer, 10 μL, 30 μL, and 100 μL of an aqueous solution of propionic acid bacteria whey fermentation product or distilled water were added to each of the Magnus tube (at final concentrations of 0.01, 0.03, and 0.10 w/v %), and the measurement of tension and observation of muscle conditions were carried out for 15 minutes. Tension measurement charts were recorded using a recorder adjusted such that a 5 cm displacement occurs per tension of 1 g on the measurement charts. The resulting measurement charts were used to observe peaks of tension associated with muscle contraction. The contraction frequency (times/minute) was calculated from the number of peaks (times) that appeared per unit time (minute), the contractile force (g) was calculated from the peak height (cm), and numerical values were used for evaluation. FIG. 1 shows representative measurement charts obtained upon addition of the propionic acid bacteria whey fermentation product.

Results

The determined contraction frequency and contractile force of each part of the colon are shown in Table 2.

TABLE 2

|  |  | AMOUNT OF TEST SUBSTANCE AQUEOUS SOLUTION ADDED (μL) | CONTRACTILE FORCE (g) | CONTRACTION FREQUENCY (TIMES/MINUTE) |
| --- | --- | --- | --- | --- |
|  | ADDED SUBSTANCE |  |  |  |
| PROXIMAL COLON mean ± SD | DISTILLED WATER n = 6 | 0 | 1.25 ± 0.43 | 0.47 ± 0.13 |
|  |  | 10 | 1.32 ± 0.43 | 0.50 ± 0.11 |
|  |  | 30 | 1.42 ± 0.48 | 0.47 ± 0.07 |
|  |  | 100 | 1.48 ± 0.40 | 0.53 ± 0.16 |
|  | PROPIONIC ACID BACTERIA FERMENTATION PRODUCT n = 6 | 0 | 1.24 ± 0.40 | 0.53 ± 0.13 |
|  |  | 10 | 1.28 ± 0.30 | 0.58 ± 0.14 |
|  |  | 30 | 1.38 ± 0.39 | 0.56 ± 0.09 |
|  |  | 100 | 1.39 ± 0.46 | 0.58 ± 0.14 |
| MIDDLE COLON mean ± SD | DISTILLED WATER n = 6 | 0 | 0.72 ± 0.21 | 0.56 ± 0.09 |
|  |  | 10 | 0.68 ± 0.21 | 0.58 ± 0.17 |
|  |  | 30 | 0.60 ± 0.14 | 0.61 ± 0.14 |
|  |  | 100 | 0.74 ± 0.14 | 0.53 ± 0.07 |
|  | PROPIONIC ACID BACTERIA FERMENTATION PRODUCT n = 6 | 0 | 0.70 ± 0.11 | 0.50 ± 0.21 |
|  |  | 10 | 0.68 ± 0.14 | 0.53 ± 0.19 |
|  |  | 30 | 0.69 ± 0.13 | 0.53 ± 0.19 |
|  |  | 100 | 0.72 ± 0.13 | 0.58 ± 0.14 |
| DISTAL COLON mean ± SD | DISTILLED WATER n = 4 | 0 | 0.83 ± 0.41 | 0.67 ± 0.14 |
|  |  | 10 | 0.80 ± 0.34 | 0.75 ± 0.29 |
|  |  | 30 | 0.96 ± 0.66 | 0.75 ± 0.10 |
|  |  | 100 | 0.92 ± 0.55 | 0.79 ± 0.16 |
|  | PROPIONIC ACID BACTERIA FERMENTATION PRODUCT n = 7 | 0 | 0.83 ± 0.28 | 0.74 ± 0.43 |
|  |  | 10 | 0.80 ± 0.24 | 0.90 ± 0.38 |
|  |  | 30 | 0.87 ± 0.25 | 1.24 ± 0.27 ** |
|  |  | 100 | 1.02 ± 0.38 | 1.31 ± 0.22 ** |

In this table, ** indicates that there is a significant difference of p<0.01 for the colon specimen versus a same volume of distilled water (Student's t-test).

The contraction frequency of the distal colon increased by addition of the propionic acid bacteria whey fermentation product in a dose dependent manner, while the contraction frequencies of the proximal colon and the middle colon did not show any change even when the propionic acid bacteria whey fermentation product was added. When 30 µL or 100 µL of the aqueous solution of propionic acid bacteria whey fermentation product was added, the contraction frequency showed a significantly higher value (p<0.01, Student's t-test) as compared to when a same volume of distilled water was added.

No change was observed for the contractile force by the addition of propionibacterial whey fermentation product in any part of the colon. In other words, the propionic acid bacteria whey fermentation product has neither a contractile force-increasing effect nor a contractile force-suppressing effect. Thus, the propionic acid bacteria whey fermentation product was found to have an activity of increasing the contraction frequency in a distal colon-specific manner, but not to have any activity of increasing the contractile force in any part.

Example 4

Efficacy of Propionic Acid Bacteria Whey Fermentation Product in Patients with Constipation-type Irritable Bowel Syndrome Method A double-blind crossover test was conducted on 12 patients with constipation-type irritable bowel syndrome (three males and nine females, aged 27 to 77). The propionic acid bacterium whey fermentation product produced by the method described in Example 1% was heat-sterilized, and dried. Tablets containing 0.2 g of this per three tablets ("active") were orally fed to six individuals randomly selected from the subjects described above, three times per day and three tablets per ingestion, i.e. a total of nine tablets per day, for four weeks (28 days). The other six individuals were orally fed with tablets containing freeze-dried product from unfermented reconstituted whey powder instead of the propionic acid bacteria whey fermentation product ("placebo"), at three tablets per day for four weeks (28 days) [early ingestion period]. Ingestion of the tablets described above was discontinued for the subsequent four weeks (28 days) for all twelve subjects [ingestion discontinuation period]. Then, for the subsequent four weeks (28 days), subjects were orally fed with three tablets per ingestion, three times per day, i.e. a total of nine tablets per day. Here, those that were previously fed with "active" were fed with "placebo", and those that were previously fed with "placebo" were fed with "active" [late ingestion period].

Assessment Methods (1) Questionnaire on Symptoms

Figure 2:
FIG. 2 is a questionnaire on defecation conditions. This was used in Example 4.

A questionnaire on symptoms was requested to be filled every day during the period of tablet ingestion. FIG. 2 shows the questionnaire to be filled every day. The questioned items relate to defecation conditions. The specific questioned items were: defecation frequency, stool property, severity of abdominal pain, sensation of incomplete evacuation and degree of straining at the time of defecation, and abdominal condition. The stool property was graded using scores based on the drawings and description shown in FIG. 2. Meanwhile, the severity of abdominal pain (presence of abdominal pain), the level of abdominal bloating having a sensation of abdominal bloating), the sensation of incomplete evacuation and the degree of straining at the time of defecation (having a sensation of incomplete evacuation, requiring straining at the time of defecation), and abdominal condition (today's total abdominal score) were graded using a visual analogue scale. Results of the visual analogue scales were obtained by measuring the length from "none" or "very bad" on one end of the scale to the mark written by the subject, and calculating the value obtained by dividing this length by the entire scale length. After collecting the questionnaires, the numerical values for the ingestion periods from day 1 to day 28 and from day 15 to day 28 were tallied according to "placebo" and "active". The mean, standard deviation, and P value (placebo vs. active, Student's t-test) were calculated for each item.

Furthermore, the questionnaire shown in FIG. 3 was requested to be filled on the last day of the early ingestion period and the last day of the late ingestion period. Here, the questioned items related to the general abdominal condition. The specific questioned items were: abdominal condition compared to before the ingestion period (degree of general improvement) and abdominal condition compared to the previous ingestion period with the other tablet (comparison between the early and late periods). In these assessments, one out of those shown in FIG. 3 was selected. The degree of general improvement includes evaluation in five levels: "considerably improved (very effective)", "improved (effective)", "no change (unaltered)", "worsened", and "considerably worsened". After collecting the questionnaires, the number of answers was determined for each level according to "placebo" and "active". Then, the proportion of respondents who answered "very effective" or "effective" was calculated as effective rate (%). Statistic analysis was carried out by cumulative chi-square test. Meanwhile, the comparison between the early and late periods (before-and-after comparison) included a three level evaluation: "better in the early period", "no change", and "better in the late period". After collecting the questionnaires, the number of answers was determined for each level according to "placebo" and "active".

(2) SF-36 Questionnaire

SF-36 (MOS Short-Form 36-Item Health Survey) questionnaire is known as a comprehensive scale that is scientifically reliable and relevant in measuring the health-related QOL. It is simple, useful, and easily available. Because of sufficient amount of already accumulated data, SF-36 questionnaire is most commonly used in the world as a health status measuring questionnaire. Specifically, using 36 questions, QOL is measured in the eight areas (subscales) listed below to comprehensively assess the QOLs of all subjects.

1) Physical functioning [PF]
2) Role physical [RP]
3) Bodily pain [BP]
4) General health perceptions [GH]
5) Vitality [VT]
6) Social functioning [SF]
7) Role emotional [RE]
8) Mental health [MH]

The present inventors conducted the test according to the description in "SF-36v2™Manual, Japanese Edition", Fukuhara, S, and Suzukamo Y., Kenko Iryo Hyokakenkyu Kikou (Institute for health outcomes and process evaluation research), 2004.

SF-36 questionnaires were requested to be filled out before early and late ingestion periods and on the last day of the early and late ingestion periods. Then, the questions on the eight areas listed above were scored by conversion into scores according to scoring based on national standard values (Norm-based scoring, NBS). These scores are obtained by re-calculating the eight subscale scores, shown in a range of 0 to 100 points, so that the national standard value of the entire Japanese public is 50 points and the standard deviation is 10 points. The national standard value refers to an average SF-36 score obtained by a national survey in which sampling is carried out such that the distribution is the same as the national distribution in terms of gender, age, geographic area, city size, and the like.

This test determined the numbers of cases with improved, unaltered, or worsened scores when scores before and after each of the ingestion periods were compared. Furthermore, the change in each score before and after each ingestion period was calculated to assess the influence of "active" or "placebo" administration.

Results (1) Results Obtained from Questionnaires on Symptoms are Shown in Tables 3 and 4.

As shown in Table 4, regarding the degree of general improvement, the effective rates were 25% and 67% with "placebo" and "active" administrations, respectively, and of the two groups, the "active" group showed a tendency for improvement ($p<0.10$; cumulative chi square test).

Furthermore, in eight of the twelve cases, the answer stated that the "active" ingestion was better than the "placebo" ingestion. There were three cases where the answer stated that "placebo" was better. One case reported that there was no difference. Furthermore, there was no significant difference between the early and late ingestion periods.

TABLE 3

RESULTS OF QUESTIONNAIRE ON SYMPTOMS

| | INGESTION PERIOD | | | | | | | | |
|---|---|---|---|---|---|---|---|---|---|
| | DAY 1 TO 28 | | | | DAY 15 TO 28 | | | | |
| | placebo | | active | | Student's t-test | placebo | | active | | Student's t-test |
| | mean | SD | mean | SD | p value | mean | SD | mean | SD | p value |
| DEFECATION FREQUENCY (PER DAY) | 0.87 | 0.51 | 1.00 | 0.63 | 0.092# | 0.82 | 0.48 | 1.09 | 0.88 | 0.082# |
| STOOL CONSISTENCY | 3.58 | 0.88 | 3.43 | 1.03 | 0.284 | 3.58 | 0.94 | 3.59 | 1.20 | 0.486 |
| ABDOMINAL PAIN | 2.61 | 1.71 | 2.46 | 1.98 | 0.280 | 2.64 | 1.70 | 2.33 | 2.07 | 0.108 |
| SENSATION OF ABDOMINAL BLOATING | 5.63 | 1.64 | 4.80 | 2.15 | 0.104 | 5.64 | 1.98 | 4.72 | 2.18 | 0.089# |
| SENSATION OF INCOMPLETE EVACUATION | 4.97 | 2.09 | 4.27 | 2.17 | 0.033* | 5.15 | 2.29 | 4.08 | 2.33 | 0.008** |
| OVERALL SCORE | 4.64 | 1.08 | 5.05 | 1.15 | 0.041* | 4.57 | 1.01 | 5.22 | 1.10 | 0.038* |

As shown in Table 3, the mean (mean), standard deviation (SD), and p value (Student's t-test) of each of the evaluation values were determined for the ingestion periods from day 1 to day 28, and day 15 to day 28, and "placebo" and "active" were compared. In Table 3, # represents $p<0.10$; * represents $p<0.05$; and ** represents $p<0.01$. For day 1 to day 28 of ingestion, "active" showed a significant improving effect on the sensation of incomplete evacuation and the overall abdominal score, with $p<0.05$ as compared to "placebo". In addition, the defecation frequency showed a tendency for improvement ($p<0.10$; Student's t-test). Further, for day 15 to day 28 of ingestion, "active" showed a significant improving effect on the sensation of incomplete evacuation and the overall abdominal score, with $p<0.01$ and $p<0.05$, respectively, as compared to "placebo" (Student's t-test). In addition, the defecation frequency and sensation of abdominal bloating showed a tendency for improvement ($p<0.10$; Student's t-test).

TABLE 4

DEGREE OF GENERAL IMPROVEMENT (COMPARED TO PERIOD WITH NO INGESTION)

| (n) | VERY EFFECTIVE | EFFECTIVE | NO CHANGE | EFFECTIVE RATE |
|---|---|---|---|---|
| PLACEBO | 1 | 3 | 8 | 25% |
| ACTIVE | 0 | 8 | 4 | 67%# |

BEFORE-AND-AFTER COMPARISON

| (n) | "ACTIVE" WAS GOOD | "PLACEBO" WAS GOOD | NO CHANGE |
|---|---|---|---|
| | 8 | 3 | 1 |

Figure 4:
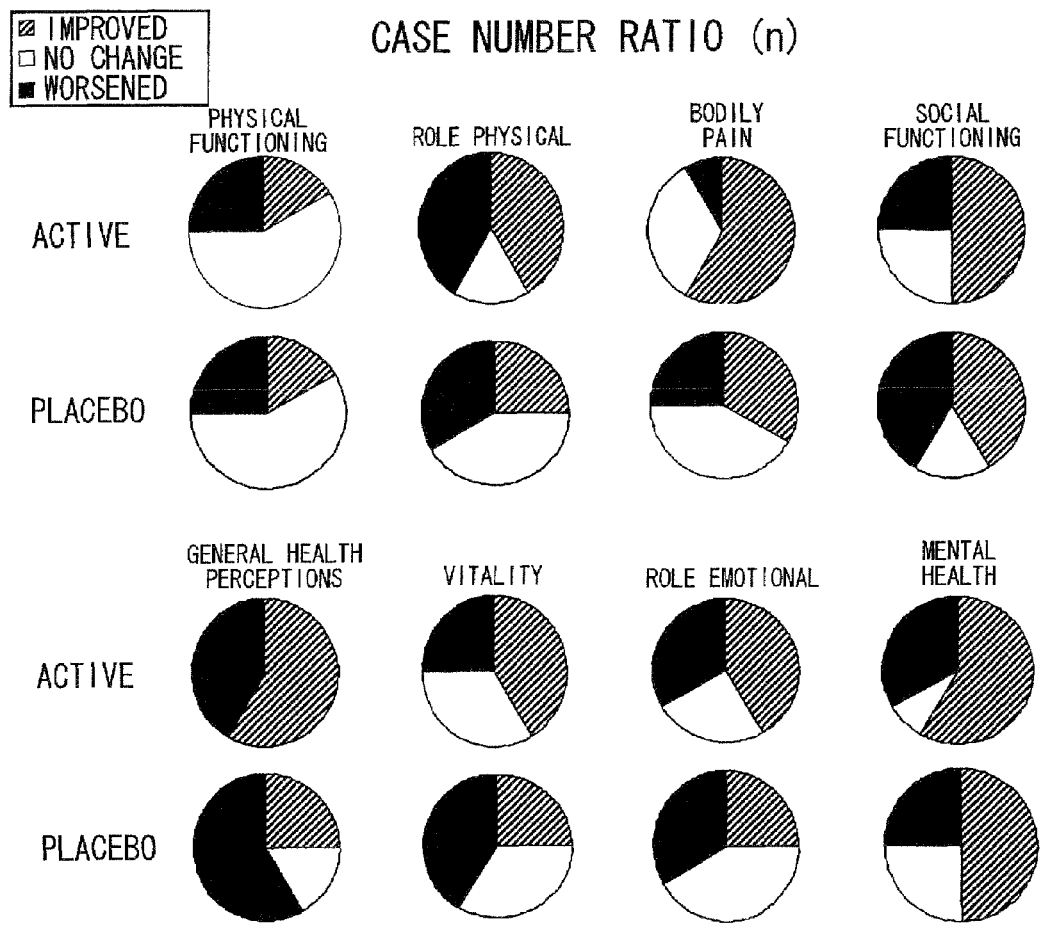
FIG. 4 shows the result of the SF-36 questionnaire of Example 4. For scores of each area, the comparison of before and after "active" intake is shown in the upper row, and the comparison of before and after "placebo" intake is shown in the lower row as ratio of case numbers (improvement in score was observed: "Improved" (shaded); no change was observed: "No change" (open square)); worsening was observed: "Worsened" (closed square)).
Figure 5:
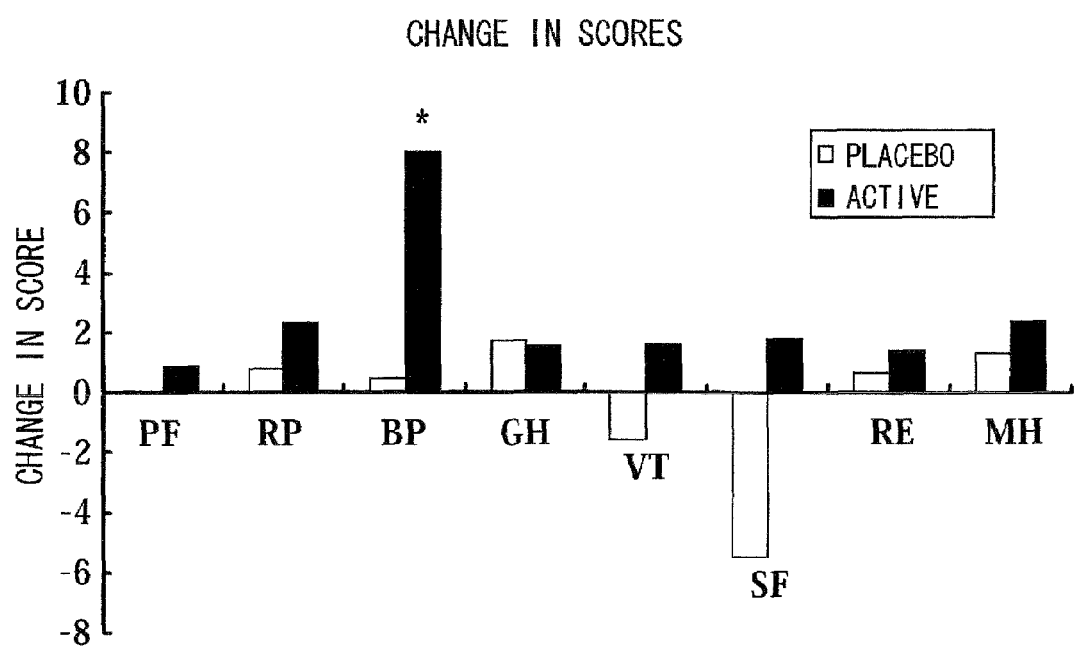
FIG. 5 shows the result of the SF-36 questionnaire of Example 4. The change of scores before and after intake was determined for each area, and the difference between before and after intake was assessed for "placebo" (open square) and "active" (closed square). *: $p<0.05$ (Student's t-test)

$p < 0.10$ by Cummulative qui square test (2) Results of the SF-36 Questionnaire are Shown in FIGS. 4 and 5.

The upper row of FIG. 4 shows a comparison of scores before and after "active" administration as case number ratio, while the lower row shows a comparison of scores before and after "placebo" administration as case number ratio. In the "active" group, many cases with overall improved scores were seen as compared to the "placebo" group, and in particular, many cases with improved bodily pain and general health were seen.

FIG. 5 shows changes in the scores before and after administration. Specifically, the score before administration was subtracted from the score after administration for the "placebo" and "active", and the calculated values were assessed as changes in the scores. Scores were found to increase overall with the "active" administration, while decreased items were found in the "placebo" group. The score for bodily pain [BP] significantly increased in "active" as compared to "placebo" ($p<0.05$; Student's t-test). Therefore, the results showed that the agents of the present invention for preventing and/or treating functional gastrointestinal disorders improve physical functioning. In addition to this, "active" ingestion showed a tendency of improving vitality [VT] and social functioning [SF] which was worsened upon "placebo" ingestion. Thus, the results showed that the agents of the present invention for preventing and/or treating functional gastrointestinal disorders improve mental functioning. These results demonstrated that, for both the physical and mental functioning aspects, the QOLs of patients with irritable bowel syndrome are improved by the ingestion of the agents of the present invention for preventing and/or treating functional gastrointestinal disorders.

Example 5

Effects of Sodium Propionate and Sodium Acetate in the Propionic Acid Bacteria Whey Fermentation Product on Intestinal Smooth Muscles The propionic acid bacterium whey fermentation product prepared in Example 1 and tested in Examples 2 and 3 contains propionic acid and acetic acid at a concentration of 0.1 mol/L each. Experiments were conducted according to Example 2 to assess whether these organic acids influence the test results.

Preparation of Colon Specimens

Seven-week-old SD type male rats were reared and habituated for one week, then sacrificed to excise the colon. Then, about 1 cm of the longitudinal muscle of the colon was isolated from the distal colon (a portion at about 2 to 3 cm to the appendix side from the anus), and cut into two pieces in the longitudinal layer direction (hereinafter, this is also referred to as colon specimen). Each colon specimen was hung with resting tension of 1 g in a Magnus tube filled with Krebs buffer under the condition described below, and a mixed gas of 95% oxygen and 5% carbon dioxide was passed thereto. Then, the colon specimens were equilibrated for about one hour while changing the Krebs buffer every 15 minutes.

Composition of Krebs Buffer:

Distilled water was added to 6.92 g of NaCl, 0.35 g of KCl, 0.29 g of $MgSO_4 \cdot 7H_2O$, 0.16 g of $KH_2PO_4$, 2.1 g of glucose, 0.28 g of $CaCl_2$, and 2.1 g of $NaHCO_3$ to obtain 1 L.

Temperature of Krebs buffer in the Magnus tube: 32° C.

Volume of Krebs buffer introduced into the Magnus tube: 10 mL.

Preparation of Test Substances

Distilled water was added to sodium propionate and sodium acetate to prepare a 0.1 mol/L sodium propionate aqueous solution and a 0.1 mol/L sodium acetate aqueous solution, which correspond to the concentrations in the propionic acid bacteria whey fermentation product. These were used as test substance aqueous solutions in the assessment test described below. Meanwhile, distilled water was used as control.

Assessment Test for the Propionic Acid Bacteria Whey Fermentation Product

After changing the Krebs buffer, 10 μL, 30 μL, and 100 μL of the 0.1 M sodium propionate aqueous solution, 0.1 M sodium acetate aqueous solution, or distilled water were added to each of the Magnus tubes. The measurement of tension and observation of muscle conditions were carried out for 15 minutes. Tension measurement charts were recorded using a recorder adjusted such that a 5 cm displacement occurs per tension of 1 g on the measurement charts. The resulting measurement charts were used to observe peaks of tension associated with muscle contraction. The contraction frequency (times/minute) was calculated from the number of peaks (times) that appeared per unit time (minute), the contractile force (g) was calculated from the peak height (cm), and numerical values were used for evaluation. With the obtained results, comparisons between the groups were further assessed for significant differences by the Student's t-test.

Results

The results of contraction frequency and contractile force are shown in Table 5.

TABLE 5

| ADDED SUBSTANCE | AMOUNT OF TEST SUBSTANCE AQUEOUS SOLUTION ADDED (μL) | CONTRACTILE FORCE (g) | CONTRACTION FREQUENCY (TIMES/MINUTE) |
|---|---|---|---|
| DISTILLED WATER | 0 | 1.01 ± 0.30 | 0.78 ± 0.38 |
| n = 6 | 10 | 0.96 ± 0.19 | 0.81 ± 0.36 |
|  | 30 | 0.95 ± 0.41 | 0.72 ± 0.40 |
|  | 100 | 1.00 ± 0.21 | 0.72 ± 0.27 |
| SODIUM PROPIONATE | 0 | 1.21 ± 0.85 | 0.70 ± 0.49 |
| n = 5 | 10 | 1.15 ± 0.72 | 0.47 ± 0.14 |
|  | 30 | 1.24 ± 0.77 | 0.73 ± 0.19 |
|  | 100 | 1.20 ± 0.68 | 0.73 ± 0.38 |
| SODIUM ACETATE | 0 | 1.53 ± 0.77 | 0.71 ± 0.52 |
| n = 7 | 10 | 1.33 ± 0.44 | 0.79 ± 0.52 |
|  | 30 | 1.20 ± 0.42 | 0.81 ± 0.63 |
|  | 100 | 1.14 ± 0.43 | 0.98 ± 0.67 |

No change was observed after addition of any of the test substances for the contraction frequency. In other words, sodium propionate and sodium acetate included in the propionic acid bacteria whey fermentation product have neither a contraction frequency-enhancing effect nor a contraction frequency-suppressing effect.

No change was observed after addition of any of the test substances for the contractile force. In other words, sodium propionate and sodium acetate included in the propionic acid bacteria whey fermentation product have neither a contractile force-increasing effect nor a contractile force-suppressing effect.

INDUSTRIAL APPLICABILITY

The present invention has an effect of preventing and/or treating functional gastrointestinal disorders, and thus is applicable as pharmaceuticals or food or beverages having the same functions.

The invention claimed is:

1. A method for treating a human patient with constipation type-irritable bowel syndrome without organic gastrointestinal disease, wherein said method comprises:
   determining whether the patient has an organic abnormality and a decrease in peristalsis in the whole colon with spastic constipation;
   determining that the patient suffers from constipation type-irritable bowel syndrome without organic gastrointestinal disease if the patient has no organic abnormality, but has a decrease in peristalsis in the whole colon with spastic constipation; and orally administering an effective amount of a whey fermentation product of *Propionibacterium freudenreichii* ET-3 (FERM BP-8115) to the patient for 15 to 28 days;

wherein the oral administration of the whey fermentation product of *Propionibacterium freudenreichii* ET-3 (FERM BP-8115) to the patient for 15 to 28 days increases the intestinal contraction frequency of the patient without changing the intestinal contractile force of the patient, thereby treating constipation type-irritable bowel syndrome in the patient.

2. The method of claim 1, wherein the whey fermentation product is prepared from a culture medium containing a nutrient source selected from the group consisting of whey, a whey protein concentrate (WPC), a whey protein isolate (WPI), and an enzyme-treated product thereof.

3. The method of claim 2, wherein the nutrient source is an enzyme-treated product of whey.

4. The method of claim 2, wherein the whey fermentation product is heat-sterilized or dried when being prepared.

* * * * *

UNITED STATES PATENT AND TRADEMARK OFFICE
CERTIFICATE OF CORRECTION

PATENT NO. : 9,675,647 B2  
APPLICATION NO. : 12/523010  
DATED : June 13, 2017  
INVENTOR(S) : Masayuki Uchida et al.

Page 1 of 1

It is certified that error appears in the above-identified patent and that said Letters Patent is hereby corrected as shown below:

In the Specification

Column 9,  
Line 22, "normal colonico" should read -- normal colonic --.

Column 13,  
Line 56, "y irradiation." should read -- $\gamma$ irradiation. --.

Column 16,  
Line 6, "y irradiation." should read -- $\gamma$ irradiation. --.

Column 17,  
Line 36, "Example 1% was" should read -- Example 1 was --.

Signed and Sealed this  
Eleventh Day of September, 2018

Andrei Iancu  
*Director of the United States Patent and Trademark Office*